United States Patent [19]

Weller, III et al.

[11] Patent Number: 5,055,466

[45] Date of Patent: Oct. 8, 1991

[54] N-MORPHOLINO DERIVATIVES AND THEIR USE AS ANTI-HYPERTENSIVE AGENTS

[75] Inventors: Harold N. Weller, III, Pennington; Denis E. Ryono, Princeton, both of N.J.

[73] Assignee: E. R. Squibb & Sons, Inc., Princeton, N.J.

[21] Appl. No.: 450,885

[22] Filed: Dec. 14, 1989

Related U.S. Application Data

[63] Continuation-in-part of Ser. No. 124,309, Nov. 23, 1987, abandoned.

[51] Int. Cl.$^5$ .................. A61K 31/38; A61K 31/415; A61K 31/44; A61K 31/495; C07D 415/00; C07D 413/12; C07D 417/12; C07D 211/68

[52] U.S. Cl. .............................. 514/235.8; 514/236.8; 514/233.8; 514/234.5; 514/237.2; 514/235.2; 514/212; 514/227.8; 514/252; 514/253; 514/255; 514/318; 514/321; 514/322; 514/326; 544/133; 544/135; 544/137; 544/139; 544/131; 544/140; 544/143; 544/58.1; 544/369; 544/368; 544/370; 544/371; 544/372; 544/360; 540/602; 540/603; 546/193; 546/194; 546/198; 546/199; 546/208; 546/209; 546/210; 546/211

[58] Field of Search .............. 544/133, 135, 137, 139, 544/140, 131, 143; 514/235.8, 236.8, 233.8, 234.5, 237.2, 235.2

[56] References Cited

U.S. PATENT DOCUMENTS

| | | | |
|---|---|---|---|
| 4,477,441 | 10/1984 | Boger et al. | 424/177 |
| 4,514,391 | 4/1985 | Gordon et al. | 514/2 |
| 4,548,926 | 10/1985 | Matsueda et al. | 514/19 |
| 4,616,088 | 10/1986 | Ryono et al. | 546/336 |
| 4,629,724 | 12/1986 | Ryono et al. | 514/18 |

FOREIGN PATENT DOCUMENTS

| | | | |
|---|---|---|---|
| 0104041 | 3/1984 | European Pat. Off. | 544/131 |
| 8403044 | 2/1986 | World Int. Prop. O. | 544/131 |

OTHER PUBLICATIONS

Toda et al., "Human Renin Inhibiting Dipeptide", European Jour. of Pharmacology, 129, 1986, 393-396.

Miyazaki et al., "Orally Active Renin Inhibiting Dipeptide", (Abstract of talk at American Society of Hypertension Conf. in New York, 1987).

Rasetti et al., "European Federation for Medicinal Chemistry's 9th Symposium on Medicinal Chemistry", West Berlin, Sep. 9-18, 1988.

S. H. Rosenberg et al., "Novel Renin Inhibitors Containing Analogues of Statine Retro-Inverted at the C-Termini: Specificity at the P$_2$ Histidine Site", *J. Med. Chem.*, 1987, vol. 30, No. 7, pp. 1224-1228.

H. L. Sham et al., "Novel Non-Basic Bioisostere of Histidine Synthesized from L-Aspartic Acid", *J. Chem. Soc., Chem. Commun.*, pp. 1792-1793 (1987).

*Primary Examiner*—Johann Richter
*Attorney, Agent, or Firm*—Theodore R. Furman, Jr.

[57] ABSTRACT

Compounds of the formula

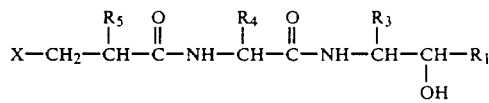

are disclosed. These compounds are inhibitors of renin and therefore useful as cardiovascular agents.

7 Claims, No Drawings

N-MORPHOLINO DERIVATIVES AND THEIR USE AS ANTI-HYPERTENSIVE AGENTS

This is a continuation-in-part of U.S. Ser. No. 124,309 filed Nov. 23, 1987, now abandoned.

FIELD OF THE INVENTION

The present invention is directed to N-heterocyclic alcohol derivatives, and more particularly concerns such compounds useful as renin inhibitors.

BACKGROUND OF THE INVENTION

Jones et al. in WO 84/03044 disclose renin inhibiting tetra-, penta-, or hexapeptide analogues of the formula $$X-D-E-A-B-Z-W$$

where X and W are terminal groups; D, E, B and Z, of which any one or, except with reduced analogues, two may be absent, are aromatic, lipophilic or (in the case of E) aromatic, lipophilic, or basic amino acid or amino acid analogue residues, and A is an analogue of a lipophilic or aromatic dipeptide residue wherein the peptide link is replaced by one to four-atom carbon or carbon-nitrogen link which as such or in hydrated form is an unhydrolyzable tetrahedral analogue of the transition state of the peptide bond as given above. In particular, A is defined as $$\begin{array}{c} R_4 \;\; R_1 \;\;\;\; R^2 \\ | \;\;\; | \;\;\;\;\;\; | \\ -N-C-M-C-G^1 \\ | \;\;\;\;\;\;\;\;\;\; | \\ R^5 \;\;\;\;\;\; R^6 \end{array}$$

wherein M can be —CH—OH.

Szelke et al. in European Patent Application 104,041 disclose renin inhibitory polypeptides including the partial sequence $$X-A-B-Z-W$$

and $$X-Phe-His-A-B-Z-W$$

wherein A is $$\begin{array}{c} R^1 \;\;\;\;\; R^3 \;\; R^2 \;\; O \\ | \;\;\;\;\;\;\;\; | \;\;\; | \;\;\; \| \\ -NH-CH-G-N-CH-C- \end{array}$$

and G is $$\begin{array}{c} OH \\ | \\ -CH-CH_2, \end{array}$$

X is hydrogen, protecting group, or an amino acyl residue, B is a lipophilic amino acyl residue, and Z plus W are an amino alcohol residue or Z is aminoacyl and W is hydroxy, ester, amide, etc.

Matsueda et al. in U.S. Pat. No. 4,548,926 disclose renin inhibiting peptides of the formula $$\begin{array}{c} \text{N} = \\ \;\;\;\;\;\;\;\;\;\; \diagdown \\ \;\;\;\;\;\;\;\;\;\;\;\;\;\; NH \\ \;\;\;\;\;\;\;\;\; / \\ \;\;\;\;\;\;\; O \;\;\;\; CH_2 \;\; O \;\;\;\;\;\;\; But \\ \;\;\;\;\;\;\; \| \;\;\;\;\;\; | \;\;\;\;\; \| \;\;\;\;\;\;\;\; | \\ R^1-C-NH-CH-C-NH-CH-X \end{array}$$

wherein But represents an isobutyl or sec-butyl group and X includes a group of the formula —CH(R$^2$)—Y.

Gordon et al. in U.S. Pat. No. 4,514,391 disclose hydroxy substituted peptide compounds of the formula $$\begin{array}{c} \;\;\;\;\;\;\;\; OH \;\;\;\;\;\; R \;\;\; R_1 \;\;\; O \\ \;\;\;\;\;\;\;\;\; | \;\;\;\;\;\;\;\;\; | \;\;\; | \;\;\;\; \| \\ R_3-CH-CH-CH_2-N-CH-C-X \\ \;\;\;\;\;\;\;\;\;\;\;\; | \\ \;\;\;\;\;\;\;\;\;\;\; NH \\ \;\;\;\;\;\;\;\;\;\;\;\; | \\ \;\;\;\;\;\;\;\;\;\;\; C=O \\ \;\;\;\;\;\;\;\;\;\;\;\; | \\ \;\;\;\;\;\;\;\;\;\;\; R_2 \end{array}$$

which possess angiotensin converting enzyme or enkephalinase inhibition activity.

A copending application, U.S. Ser. No. 003,446 entitled "N-HETEROCYCLIC ALCOHOL RENIN INHIBITORS", filed Jan. 15, 1987, discloses compounds of the formula $$\begin{array}{c} \;\;\;\;\;\;\;\;\;\;\;\; R_5 \;\; O \;\;\;\;\;\; R_4 \;\; O \;\;\;\;\;\; R_3 \\ \;\;\;\;\;\;\;\;\;\;\;\;\; | \;\;\; \| \;\;\;\;\;\;\; | \;\;\; \| \;\;\;\;\;\;\; | \\ X \!\!+\!\! NH-CH-C\!\!\!+\!\!\!\!_p NH-CH-C-NH-CH-CH-R_1 \\ \;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\; | \\ \;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\; OH \end{array}$$

wherein $R_1$ can be various N-heterocyclic moieties.

SUMMARY OF THE INVENTION

In accordance with the present invention novel compounds which are inhibitors of renin, and therefore useful as cardiovascular agents, are disclosed. These compounds have the formula $$\begin{array}{c} \;\;\;\;\;\;\;\;\;\;\;\;\;\; R_5 \;\; O \;\;\;\;\;\; R_4 \;\; O \;\;\;\;\;\; R_3 \;\;\;\;\;\;\;\;\; I \\ \;\;\;\;\;\;\;\;\;\;\;\;\;\;\; | \;\;\; \| \;\;\;\;\;\;\; | \;\;\; \| \;\;\;\;\;\;\; | \\ X-CH_2-CH-C-NH-CH-C-NH-CH-CH-R_1 \\ \;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\; | \\ \;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\; \cdot OH \end{array}$$

including pharmaceutically acceptable salts thereof, wherein X is $$\begin{array}{cc} \;\;\;\;\;\;\;\;\;\;\;\;\;\;\;\;\;\;\;\;\;\; O & \;\;\;\;\;\;\;\;\;\;\;\;\;\;\;\; O \\ \;\;\;\;\;\;\;\;\;\;\;\;\;\;\;\;\;\;\;\;\;\; \| & \;\;\;\;\;\;\;\;\;\;\;\;\;\;\;\; \| \\ R_6-(CH_2)_m-A-N-C-, & R_6-(CH_2)_m-A-C-, \\ \;\;\;\;\;\;\;\;\;\;\;\;\;\;\;\;\;\; | & \\ \;\;\;\;\;\;\;\;\;\;\;\;\;\;\;\;\;\; R_{10} & \end{array}$$

$$\begin{array}{cc} \;\;\;\;\;\;\;\;\;\;\;\;\;\;\;\;\;\;\;\;\;\; O & \\ \;\;\;\;\;\;\;\;\;\;\;\;\;\;\;\;\;\;\;\;\;\; \| & \\ R_6-(CH_2)_m-A-O-C-, & R_6-(CH_2)_m-A-S-, \end{array}$$

$$R_6-(CH_2)_m-A-SO-, \;\; R_6(CH_2)_m-A-SO_2,$$

$$\begin{array}{cc} & \;\;\;\;\;\;\;\;\;\;\;\;\;\;\;\;\;\;\;\;\;\; O \\ & \;\;\;\;\;\;\;\;\;\;\;\;\;\;\;\;\;\;\;\;\;\; \| \\ R_6-(CH_2)_m-A-N-SO_2-, & R_6-(CH_2)_m-A-C-S-, \\ \;\;\;\;\;\;\;\;\;\;\;\;\;\;\;\;\; | & \\ \;\;\;\;\;\;\;\;\;\;\;\;\;\;\;\;\; R_{10} & \end{array}$$

-continued

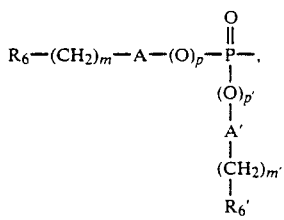 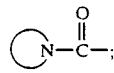

$R_1$ is a fully saturated, partially saturated, or unsaturated monocyclic N-heterocyclic ring of 5 or 6 atoms containing at least one N atom or a bicyclic ring in which such N-heterocyclic ring is fused to a benzene ring. The N-heterocyclic ring can also include an O or S atom or up to three additional N atoms. The N-heterocyclic ring is attached to $$-\overset{|}{\underset{OH}{C}}H-$$

by way of an available carbon atom. An available N atom in the N-heterocyclic ring can be substituted with an N-protecting group such as

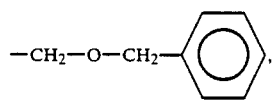

2,4-dinitrophenyl, or loweralkyl,

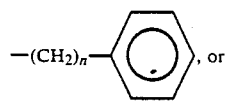, or

—$(CH_2)_n$-cycloalkyl.

Similarly, an available C atom in the monocyclic ring or an available C atom in the benzene portion of the bicyclic ring can be substituted with lower alkyl

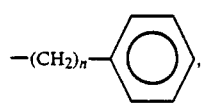, or—$(CH_2)_n$-cycloalkyl.

Preferred N-heterocyclic rings are

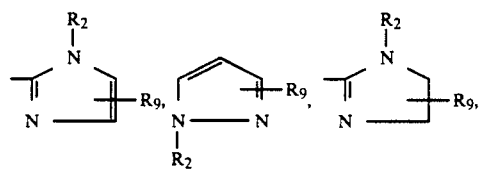

-continued

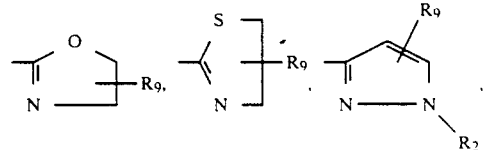

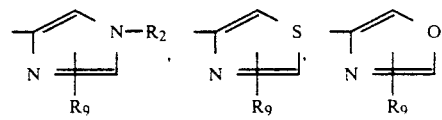

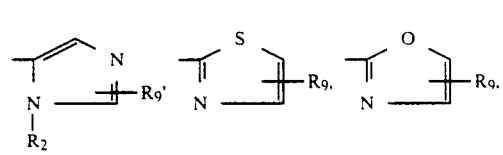

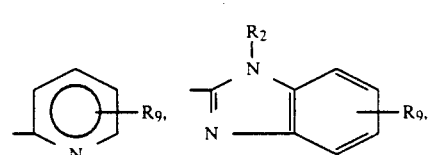

$R_2$ is

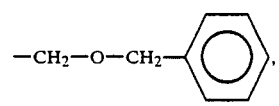

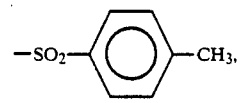

2,4-dinitrophenyl, hydrogen, lower alkyl,

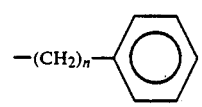

or —$(CH_2)_n$-cycloalkyl;

represents a heterocyclic ring of the formula

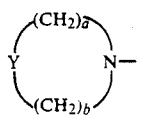

wherein Y is —CH₂, O, S, or N—R₉, a is an integer from 1 to 4, and b is an integer from 1 to 4 provided that the sum of a plus b is an integer from 2 to 5 and such heterocyclic rings wherein one carbon atom has a lower alkyl substituent;

Exemplary

groups include

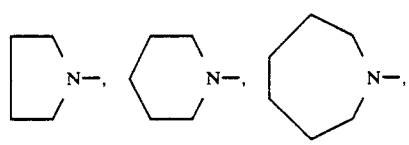

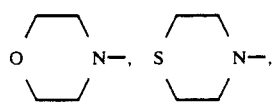

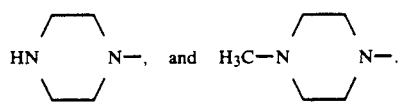

$R_3$ and $R_5$ are independently selected from hydrogen, lower alkyl, halo substituted lower alkyl, —(CH₂)ₙ-aryl, —(CH₂)ₙ-heterocyclo, —(CH₂)ₙ—OH, —(CH₂)ₙ—O—lower alkyl, —(CH₂)ₙ—NH₂, —(CH₂)ₙ—SH, —(CH₂)ₙ—S—lower alkyl, —(CH)ₙ—O—(CH₂)g—OH, —(CH₂)ₙ—O—(CH₂)g—NH₂, —(CH₂)ₙ—S—(CH₂)g—OH,

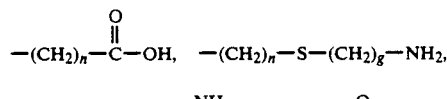

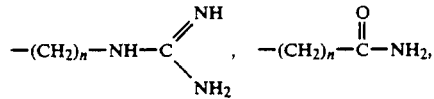

and —(CH₂)ₙ-cycloalkyl;

$R_4$ is selected from hydrogen, lower alkyl, halo substituted lower alkyl, —(CH₂)ₙ-aryl, —(CH₂)ₙ-heterocyclo, —(CH₂)ₙ—OH, —(CH₂)ₙ—O—lower alkyl, —(CH₂)ₙ—NH₂, —(CH₂)ₙ—SH, —(CH₂)ₙ—S—lower alkyl, —(CH₂)ₙ—O—(CH₂)g—OH, —(CH₂)ₙ—O—(CH₂)g—NH₂, —(CH₂)ₙ—S—(CH₂)g—OH,

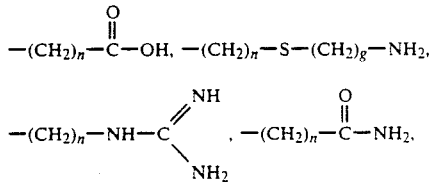

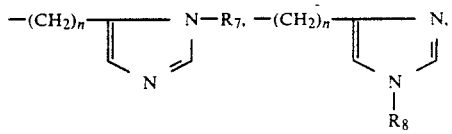

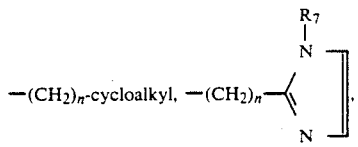

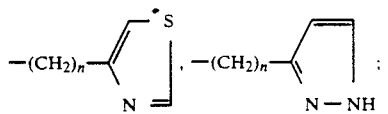

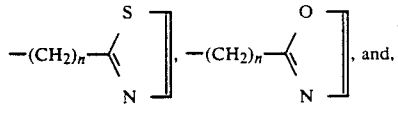

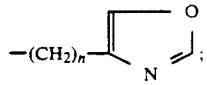

$R_6$, $R_6'$ and $R_6''$ are independently selected from hydrogen, alkyl, aryl, pyridyl and cycloalkyl, or $R_6$ and $R_6'$ taken together with the atom to which they are bonded may form a ring of 3 to 5 carbons;

m, m' and m" are zero or an integer from 1 to 5;
n is an integer from 1 to 5;
p and p' are zero or 1;
g is an integer from 2 to 5;
$R_7$ is

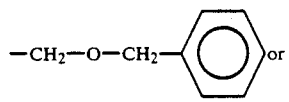

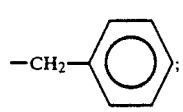

$R_8$ is 2,4-dinitrophenyl

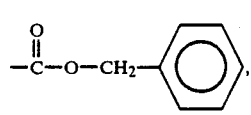

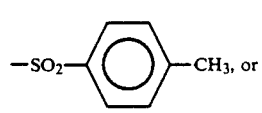

-continued

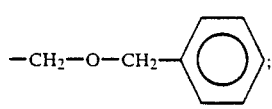

$R_9$ is hydrogen, lower alkyl, $-(CH_2)_n$ or $-(CH_2)_n$-cycloalkyl;

$R_{10}$ is $-(CH_2)_{m'}-R_6'$;

A and A' are a single bond or $-(CH)-(CH_2)_{m''}-R_6''$.

DETAILED DESCRIPTION OF THE INVENTION

This invention in its broadest aspects relates to the compounds of formula I above, to compositions and the method of using such compounds as antihypertensive agents.

The term lower alkyl used in defining various symbols refers to straight or branched chain radicals having up to seven carbons. Similarly, the terms lower alkoxy and lower alkylthio refer to such lower alkyl groups attached to an oxygen or sulfur. The preferred lower alkyl groups are straight or branched chain of 1 to 5 carbons.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkythio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are selected from methyl, methoxy, methylthio, halogen, and hydroxy.

The term heterocyclo refers to fully saturated or unsaturated rings of 5 or 6 atoms containing one or two 0 and S atoms and/or one to four N atoms provided that the total number of hetero atoms in the ring is 4 or less. The hetero ring is attached by way of an available carbon atom. Preferred hetero groups include 2-thiazolyl, 2- and 4-imidazolyl, 2- and 3-thienyl, 2- and 3-furyl, 2-, 3- and 4-pyridyl. The term hetero also includes bicyclic rings wherein the five or six membered ring containing O, S and N atoms as defined above is fused to a benzene ring. The preferred bicyclic ring is benzimidazolyl.

The compounds of formula I are prepared by coupling an amine of the formula

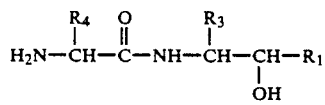

with the compound of the formula

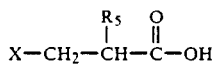

in a solvent, e.g. dimethylformamide, and in the presence of a coupling agent, e.g. dicyclohexylcarbodiimide.

To make the amine of formula II, a starting material, $H-R_1$, is treated with n-butyl lithium to obtain a compound of the formula

Compound IV is thereafter reacted with an aldehyde of the formula

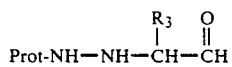

(wherein Prot is an amino protecting group, e.g. t-butoxycarbonyl) to provide the protected amine of the formula

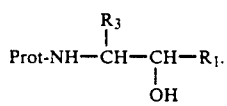

Compound VI, in a solvent such as ethyl acetate, can be deprotected by means known in the art, e.g. by treatment with hydrogen chloride, to provide an amine of the formula

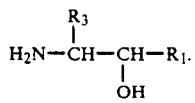

The amine of formula II can then be prepared by reacting the deprotected amine of formula VII with an N-protected amino acid of the formula

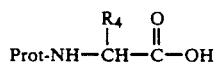

in the presence of a coupling agent, such as dicyclohexylcarbodiimide, and thereafter removing the protecting group by known means, e.g. treatment with hydrogen chloride in the case of a t-butoxycarbonyl protecting group.

To make the compounds of formula I wherein X

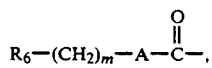

a compound of the formula

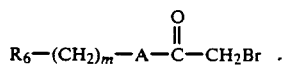

(the preparation of which has been described, for example, in *Tetrahedron Letters*, 26, 5611–5615, 1970) is coupled with a diethyl malonate derivative having the formula

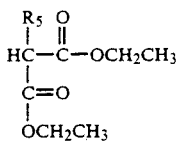   X in a solvent, e.g. tetrahydrofuran, and in the presence of a base, e.g. sodium hydride, to provide a compound of the formula

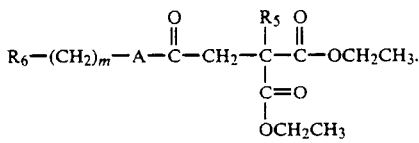   XI

Compound XI in a solvent, e.g. aqueous ethanol, is treated in a strong base, such as sodium hydroxide, and thereafter with hydrochloric acid and heat to provide the compounds of formula III where X is

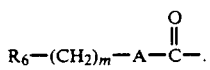

Reaction with compound II, as above, provides the corresponding compounds of formula I.

To make the compounds of formula I where X is

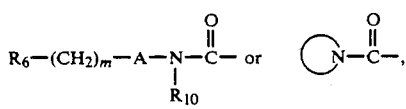

and $R_5$ is —$(CH_2)_n$-aryl and n=1, a compound of the formula

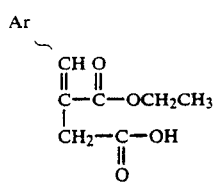   XII (the preparation of which has been described in *J Amer. Chem. Soc.*, 90, 3495, (1968)), is hydrogenated in the presence of a palladium on carbon catalyst to provide a compound having the formula

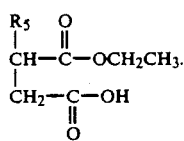   XIII

Compound XIII is reacted with a compound of the formula

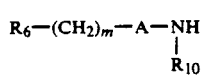   XIV or

   XV in the presence of a catalyst, such as hydrogenzotriazole, and dicyclohexylcarbodiimide to provide the ethyl ester of the formula

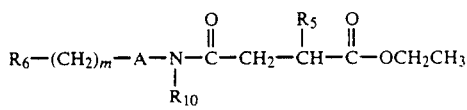   XVI or

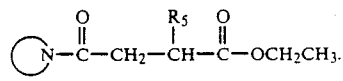   XVII

Compound XVI or XVII, in a solvent such as aqueous ethanol, is treated with a strong base, e.g. sodium hydroxide to provide the compounds of formula III wherein X is

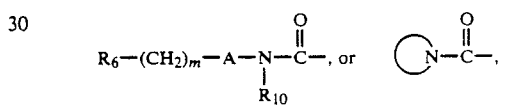

and $R_5$ is —$(CH_2)_n$-aryl and n=1. Reaction with compound II, as above, provides the corresponding compounds of formula I.

Alternatively, to make the compounds of formula I where X is

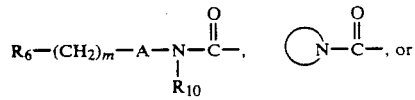

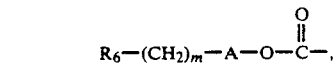

and $R_5$ is —$(CH_2)_n$-aryl and n=1 to 5, a dialkylmalonate of the formula

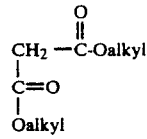   XVIII in a solvent, such as tetrahydrofuran, is treated with sodium hydride and thereafter reacted with a compound of the formula

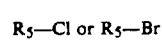   XIX to provide a compound having the formula $$\begin{array}{c} R_5 \quad O \\ | \quad \parallel \\ CH-C-Oalkyl. \\ | \\ C=O \\ | \\ Oalkyl \end{array} \qquad XX$$

Compound XX, in a solvent such as aqueous ethanol, is treated with a strong base, e.g. sodium hydroxide, and thereafter with hydrochloric acid to provide $$\begin{array}{c} R_5 \quad O \\ | \quad \parallel \\ CH_2-C-OH. \end{array} \qquad XXI$$

Compound XXI is treated with benzyl alcohol and 4-dimethylamino pyridine in a solvent, e.g. methylene chloride, in the presence of dicyclohexylcarbodiimide to provide the ester of the formula $$\begin{array}{c} R_5 \quad O \\ | \quad \parallel \\ CH_2-C-OCH_2-\text{C}_6H_5, \end{array} \qquad XXII$$

which is treated with diisopropylamine and n-butyl lithium in a solvent such as tetrahydrofuran, and thereafter reacted with t-butyl bromoacetate to provide $$\begin{array}{c} O \quad\quad R_5 \quad O \\ \parallel \quad\quad | \quad \parallel \\ t\text{-BuO}-C-CH_2-CH-C-OCH_2-\text{C}_6H_5. \end{array} \qquad XXIII$$

Compound XXIII, in a solvent, such as methylene chloride, is treated with a strong acid, e.g. trifluoroacetic acid, to provide a compound of the formula $$\begin{array}{c} O \quad\quad R_5 \quad O \\ \parallel \quad\quad | \quad \parallel \\ HO-C-CH_2-CH-C-OCH_2-\text{C}_6H_5. \end{array} \qquad XXIV$$

Compound XXIV, in a solvent, such as tetrahydrofuran, is coupled with $$R_6-(CH_2)_m-A-NH, \quad \bigcirc\!\!\!\!\!N-H$$
$$\qquad\qquad\qquad\qquad | \\ \qquad\qquad\qquad\qquad R_{10}$$

or $R_6-(CH_2)_m-A-OH$ in the presence of a catalyst, such as hydroxybenzotriazole or dimethylaminopyridine, and dicyclohexylcarbodiimide to provide the compounds of formula III where X is $$R_6-(CH_2)_m-A-N-\overset{O}{\underset{\parallel}{C}}-, \quad \bigcirc\!\!\!\!\!N-\overset{O}{\underset{\parallel}{C}}-, \text{ or}$$
$$\qquad\qquad\qquad | \\ \qquad\qquad\qquad R_{10}$$

$$R_6-(CH_2)_m-A-O-\overset{O}{\underset{\parallel}{C}}-$$

and $R_5$ is $-(CH_2)_n$-aryl and n=1 to 5. Reaction with compound II, as above, provides the corresponding compounds of formula I.

To make the compounds of formula I where X is $R_6-(CH_2)_m-A-S-$, a compound of the formula $$\begin{array}{c} O \quad R_5 \quad O \\ \parallel \quad | \quad \parallel \\ HO-C-CH-C-OH \end{array} \qquad XXV$$

is reacted with dimethylamine in the presence of formaldehyde to provide a compound of the formula $$\begin{array}{c} O \quad R_5 \quad O \\ \parallel \quad | \quad \parallel \\ HO-C-C-C-OH. \\ \quad\quad | \\ \quad\quad CH_2 \\ \quad\quad | \\ \quad\quad N \\ \quad / \quad \backslash \\ CH_3 \quad\quad CH_3 \end{array}$$

Compound XXVI is heated to provide the acrylic acid of the formula $$\begin{array}{c} R_5 \quad O \\ | \quad \parallel \\ H_2C=C-C-OH. \end{array}$$

Compound XXVII, in a solvent such as piperidine, is reacted with a compound of the formula $$R_6-(CH_2)_m-A-SH \qquad XXVIII$$

to provide $$\begin{array}{c} R_5 \quad O \\ | \quad \parallel \\ R_6-(CH_2)_m-A-S-CH_2-CH-C-OH, \end{array} \qquad XXIX$$

that is, the compounds of formula III wherein X is $R_6-(CH_2)_m-A-S-$. Reaction with compound II, as above, provides the corresponding compounds of formula I.

Alternatively, a compound of the formula XXVII may be esterified by reaction with ethanol in the presence of dicyclohexylcarbodiimide and a catalyst such as dimethylaminopyridine to give a compound of the formula $$\begin{array}{c} R_5 \quad O \\ | \quad \parallel \\ H_2C=C-C-OCH_2CH_3. \end{array} \qquad XXVIIa$$

Compound XXVIIa, in a solvent such as ethanol is then reacted with a compound of the formula XXVIII in the presence of a base such as sodium ethoxide to give a compound of the formula $$\begin{array}{c} R_5 \quad O \\ | \quad \parallel \\ R_6-(CH_2)_m-A-S-CH_2-CH-C-OCH_2CH_3. \end{array} \qquad XXIXa$$

Compound XXIXa is treated with sodium hydroxide to give compound XXIX.

When X is $R_6-(CH_2)_m-A-SO-$, compound XXIX in a solvent, e.g. methanol, is treated with hydrogen peroxide. When X is $R_6-(CH_2)_m-A-SO_2-$, compound XXIX, in a solvent such as methanol, is treated with potassium monopersulfate. The resulting species of formula III can be reacted with compound II, as above, to provide the compounds of formula I wherein X is $R_6-(CH_2)_m-A-SO-$ and $R_6-(CH_2)_m-A-SO_2-$, respectively.

To make the compounds of formula I where X is

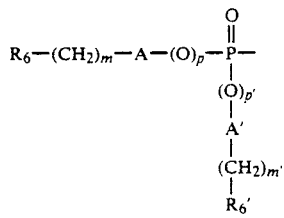

and p and p' are 1, a compound of the formula

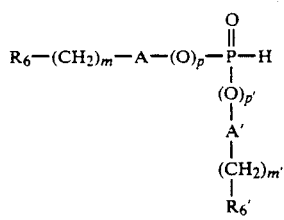   XXX is reacted with the acrylic acid of formula XXVII in dichloromethane and in the presence of bis(trimethylsilyl)acetamide to provide the compound of formula III where X is

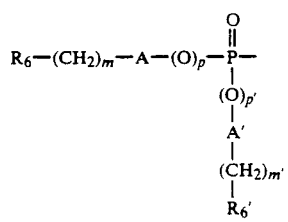

Reaction with compound II, as above, provides the corresponding compounds of formula I.

To make the compounds of formula I where X is

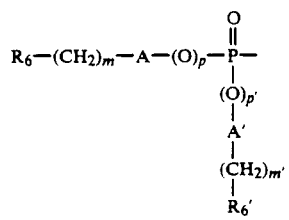

and p and/or p' are 0, a compound of the formula XXX wherein p and p' are 1 is reacted with a compound of the formula

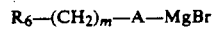   XXXI

The resulting species is then reacted with the acrylic acid of the formula XXVII to provide the compound of the formula III where X is

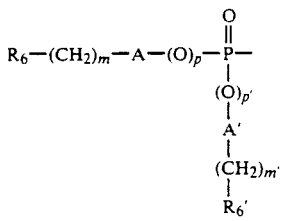

and either p or p' or both are 0. Reaction with compound II, as above, provides the corresponding compounds of formula I.

To make compounds of the formula I where X is

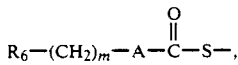

a compound of the formula

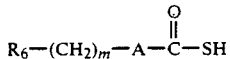   XXXII is reacted with an acrylic acid of formula XXVII to give a compound of the formula

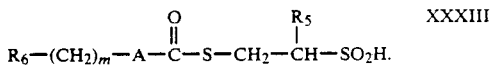   XXXIII

Reaction of compound XXXIII with compound II, as above, provides the corresponding compounds of formula I.

To make compounds of the formula I where X=HS, a compound of the formula I where X=

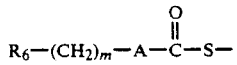

is treated with ammonium hydroxide solution.

To make the compounds of the formula I where X=

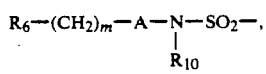

a compound of formula XXXIII is treated with ammonium hydroxide solution to give a compound of the formula

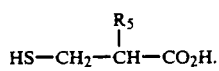   XXXIV

The compound of formula XXXIV is esterified, for example, by treatment with ethanol and dicyclohexylcarbodiimide in the presence of a catalyst, such as dimethylaminopyridine, to give a compound of formula

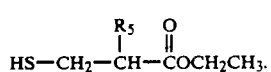   XXXV

The compound XXXV is treated with chlorine gas in a solvent such as aqueous acetic acid, to give the compound

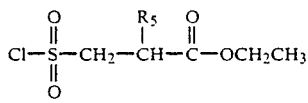 XXXVI which is reacted with an amine

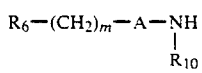 XXXVII to give a compound of the formula

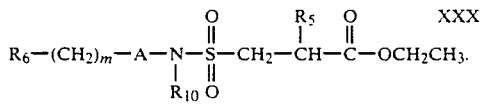 XXXVIII

Compound XXXVIII is saponified with a strong base, such as sodium hydroxide, to give a compound of the formula

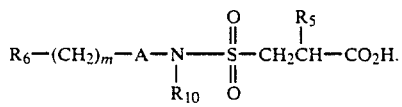 XXXIX

Reaction of compound XXXIX with compound II, as above, provides the corresponding compounds of formula I.

In the above reactions, if any of $R_3$, $R_4$ and $R_5$ are —$(CH_2)_n$-aryl wherein aryl is phenyl, 1-naphthyl, 2-naphthyl substituted with one or more hydroxy or amino groups, —$(CH_2)_n$-heterocyclo wherein heterocyclo is an imidazolyl, —$(CH_2)_n$—$NH_2$, —$(CH_2)_n$—SH, —$(CH_2)_n$—OH,

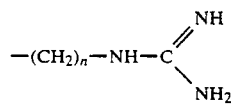

or

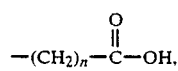

then the hydroxyl, amino, imidazolyl, mercaptan, carboxyl, or quanidinyl function should be protected during the reaction. Suitable protecting groups include benzyloxycarbonyl, t-butoxycarboxyl, benzyl, benzhydryl, trityl, tosyl, etc., and nitro in the case of guanidinyl. The protecting group is removed by hydrogenation, treatment with acid, or by other known means following completion of the reaction.

The various peptide intermediates employed in above procedures are known in the literature or can be readily prepared by known methods. See for example, the Peptides, Volume 1, "Major Methods of Peptide Bond Formation", Academic Press (1979).

Preferred compounds of this invention are those of formula I wherein

X is

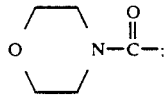

$R_1$ is

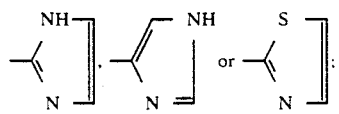

$R_3$ is straight or branched chain lower alkyl of 3 to 5 carbons, —$(CH_2)_n$-cyclopentyl, —$(CH_2)_n$-cyclohexyl, or

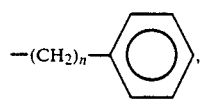

wherein n is an integer from 1 to 3;

$R_4$ is hydrogen, straight or branched chain lower alkyl of up to 5 carbons, —$(CH_2)^o$ —$NH_2$,

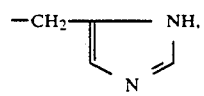

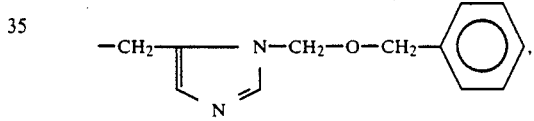

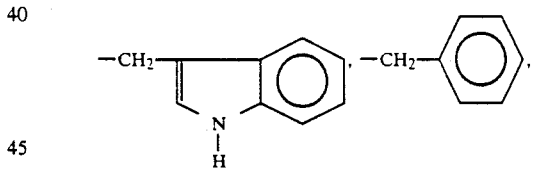

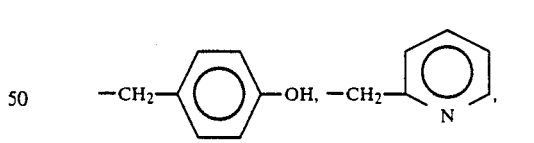

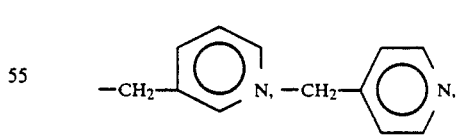

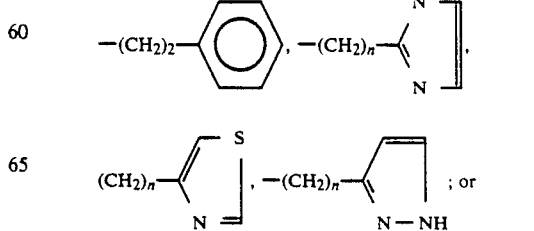

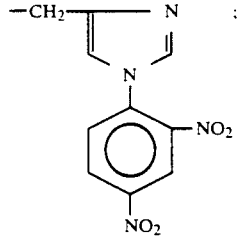

$R_5$ is straight or branched chain lower alkyl of up to 5 carbons,

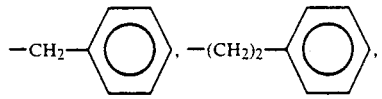

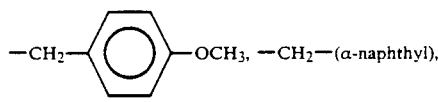

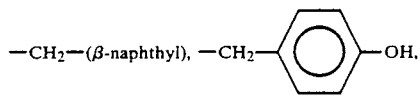

—CH$_2$-cyclopentyl, —CH$_2$-cyclohexyl,

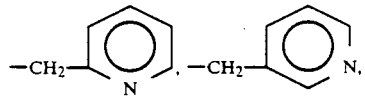

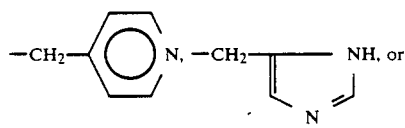

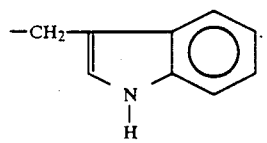

Most preferred are those compounds of formula I wherein
$R_6$ is cycloalkyl, morpholinyl, ethyl or ethoxy;
$R_1$ is

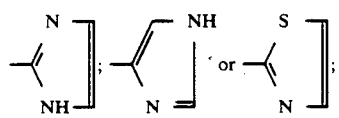

$R_3$ is

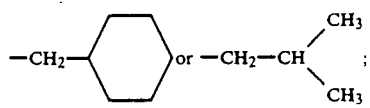

$R_4$ is

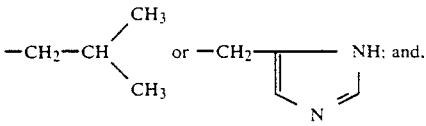

R is

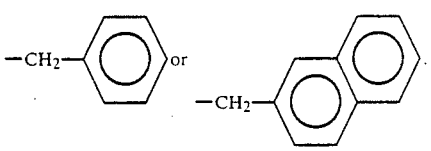

The compounds of formula I form salts with a variety of inorganic and organic acids. The nontoxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

The compounds of formula I contain asymmetric centers when any or all of $R_3$, $R_4$ and $R_5$ are other than hydrogen and at the carbon to which the —OH group is attached. Thus, the compounds of formula I can exist in diastereoisomeric forms or in mixtures thereof. The above-described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are antihypertensive agents. They inhibit the conversion of angiotensinogen to angiotensin I and therefore, are useful in reducing or relieving angiotensin related hypertension. The action of the enzyme renin on aniotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg, preferably about 250 to 500 mg per kg of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg, preferably about 3000 to 4000 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will now be described by the following examples, however, the invention should not be limited to the details therein.

EXAMPLE 1

N-[(S)-2-Cyclohexyl-1-[(R)-hydroxy(1H-imidazol-2-yl)$_m$ethyl]ethyl]-N2-[4-(4-morpholinyl)-1,4-dioxo-2-(phenylmethyl)butyl]-L-histidinamide, isomer B, dihydrochloride

A. (Phenylmethyl)butanedoic acid, 1-ethyl ester

A mixture of α-ethyl-α-benzal succinate (16.3 g, 70 mmols; prepared as described by Cohen and Milovanovic, *J. Amer. Chem. Soc.*, 90, 3495, (1968)) and 10% palladium on carbon (1.2 g) in absolute ethanol (250 mL) was hydrogenated at 30 psi on a Parr apparatus for 24 hours, after which it was filtered and concentrated. The residue was dissolved in ether, dicyclohexylamine (70 mmols) was added, and the mixture was filtered. Hexane was added to the filtrate and the crystals which formed on cooling to −30° C. were collected. The solid product was recrystallized from ethyl acetate to give the title A dicyclohexylammonium salt (10.7 g). The salt was dissolved in ethyl acetate and washed with aqueous 1N hydrochloric acid. The ethyl acetate layer was dried and concentrated. The residue was dissolved in ether and was extracted with sodium bicarbonate solution. The combined aqueous layers were acidified by addition of concentrated hydrochloric acid and extracted with ethylene acetate. The extract was dried over anhydrous magnesium sulfate and concentrated to give the title A compound as a pale yellow oil which solidified on standing overnight (6.2 g, 38% yield).

B. α-(Phenylmethyl)-γ-oxo-4-morpholinebutanoic acid, ethyl ester

To a mixture of the title A compound (3.05 g, 15 mmol) and morpholine (1.3 mL, 15 mmol) in tetrahydrofuran (50 mL) and dimethylformamide (5 mL) were added 1-hydroxybenzotriazole hydrate (2.1 g, 15 mmol) and dicyclohexylcarbodiimide (3.1 g, 15 mmol). The mixture was stirred at 25° C. for 16 hours, after which it was filtered and concentrated. The residue was dissolved in ethyl acetate, washed sequentially with 1N hydrochloric acid and saturated aqueous sodium bicarbonate solution, dried over anhydrous magnesium sulfate, and concentrated. The residue (3.6 g) was flash chromatographed on Merck silica gel (180 g), eluting with 1:1 hexane:ethyl acetate to give the title B compound as a clear, colorless oil (3.4 g, 75%), $R_f$ 0.25.

C. α-(Phenylmethyl)-γ-oxo-4-moroholinebutanoic acid

A mixture of the title B compound (3.3 g, 10.8 mmol) and 1N aqueous sodium hydroxide solution (11 mL, 11 mmol) in absolute ethanol (11 mL) was stirred for 22 hours at 25° C., after which it was concentrated in vacuo. The residue was dissolved in water, washed with ether, acidified by addition of 1N hydrochloric acid (50 mL), and extracted three times with ethyl acetate. The combined extract was dried over anhydrous magnesium sulfate and concentrated and the residue was crystallized from ethyl acetate/hexane to give the title C compound as a white solid (2 g, 67%), m.p. 133°–134° C.

D. (S)-2-[[(1,1-Dimethylethoxy)carbonyl]amino]-2-phenylmethyl-1-ethanol

To a solution containing N-[(1,1-dimethylethoxy)carbonyl]phenylalanine (10 g, 37.7 mmole) in dimethylformamide (40 ml) is added solid sodium bicarbonate (4.75 g, 56.6 mmole) and iodometbane (16 g, 113 mmole). The mixture is heated at 40° under argon for 12 hours, the cooled and the reaction mixture partitioned between water (150 ml) and ether (250 ml). The organic layer is rinsed with 2% aqueous sodium bicarbonate (2×100 ml), 2% aqueous sodium bisulfite (100 ml), water (2×100 ml), and brine, dried over magnesium sulfate, and concentrated in vacuo to give 10.5 g of N-[(1,1-dimethylethoxy)carbonyl]-L-phenylalanine, methyl ester as an oil.

To a solution containing N-[(1,1-dimethylethoxy)carbonyl]-L-phenylalanine, methyl ester (10 g, 35.8 mmole) dissolved in a mixture of tetrahydrofuran (190 ml) and absolute ethanol (190 ml) is added lithium chloride (6.09 g, 143.2 mmole). The resulting homogeneous solution is treated with sodium borohydride (5.42 g, 143.2 mmole) and the reaction is stirred at room temperature under argon for 24 hours. The reaction mixture is next filtered using ether (~700 ml) to rinse the filter cake. The resulting filtrate is rinsed with water (3×200 ml) and brine (200 ml), dried over magnesium sulfate, and concentrated in vacuo to give 9 g of crude product. Recrystallization from ether/hexane gives 7.59 g of the title D compound,; m.p. 94°–96°.

Analysis calc'd for $C_{14}H_{21}NO_3$: C, 66.90; H, 8.42; N, 5.57; Found: C, 66.80; H, 8.57; N, 5.38.

E. [(S)-2-Cyclohexyl-1-(hydroxymethyl)ethyl]carbamic acid, 1,1-dimethylethyl ester A solution of the title D compound (7 g, 27.8 mmole) in methanol (70 ml) is hydrogenated at 55 psi on a Parr Shaker using 5% rhodium on alumina (500 mg) as catalyst. After 17 hours, the reaction mixture is filtered and concentrated in vacuo to yield 7.36 g of the title E compound as an oil.

Analysis calc'd for $C_{14}H_{27}NO_3$: C, 65.33; H, 10.57; N, 5.44 Found: C, 64.94; H, 10.55; N, 5.23.

F. (S)-(2-Cyclohexyl-1-formylethyl)carbamic acid, 1,1-dimethylethyl ester

A solution of the title E compound (4.6 g, 17.9 mmole) in methylene chloride (40 ml) is added to a mixture of Dess-Martin periodinane reagent (8 g, 19 mmole) [prepared according to Dess et al., *J. Org. Chem.*, Vol. 48, p. 4155 (1983) and t-butanol (1.5 g, 19 mmole) in methylene chloride (70 ml) which had been stirred at room temperature before the addition. A slight exotherm (to 32°) results. After 30 minutes, the reaction mixture is quenched in ether (800 ml), resulting in the separation of a white solid. A mixture of sodium thiosulfate pentahydrate (31.3 g, 126 mmole) in saturated sodium bicarbonate solution (200 ml) is added, with stirring. The resulting two-phase mixture is separated and the organic phase is washed with water, saturated sodium bicarbonate (2×100 ml), water, and brine, dried over magnesium sulfate, and concentrated in vacuo to give 3.8 g of the title F compound as a colorless oil.

G. (1S)-1-(Cyclohexylmethyl)-2-hydroxy-2-[1-[(phenylmethyl)$_m$ethyl]-1H-imidazol-2-yl]-ethyl]carbamic acid, 1,1-dimethylethyl ester 2.5 M n-Butyllithium solution in hexane (12 ml, 31 mmole) is added to a solution of 1-[(phenylmethoxy)$_m$ethyl]-1H-imidazole (5.3 g. 28 mmole) in tetrahydrofuran (90 ml) at −70° under argon. After stirring for 15 minutes, the title F compound (3.6 g, 14 mmole) in tetrahydrofuran (36 ml) is added dropwise over a period of 5 minutes at a reaction temperature of −65° to −70°. After 2 hours at −70°, the bath is warmed to 0° and saturated ammonium chloride (25 ml) is added followed by ether (300 ml) and water (2×50 ml) and brine, dried over magnesium sulfate, and concentrated in vacuo. The resulting crude product (8.4 g) is flash chromatographed eluting with acetone:petroleum ether (1:4) to give 580 mg of the title G (fast moving isomer), 370 mg of a mixed fraction and 2 g of a slow moving isomer.

H. [R-(R*,S*)]-α-(1—Amino-2-cyclohexylmethyl)-1-](phenylmethoxy)methyl]-1H-imidazole-2-methanol A solution of the title G compound (3.92 g, 8.83 mmols) in ethyl acetate (200 mL) was cooled to 0° C. and hydrochloric acid gas was bubbled through the solution for 30 minutes. The mixture was then stirred for 3.5 hours as it warmed to room temperature, after which it was concentrated in vacuo to give the title H compound as a white power (3.56 g 97%).

I. L-Histidine, methyl ester, dihydrochloride

To a stirred solution (ice-bath) of L-histidine (38.75 g, 240 mmol) in methanol (500 ml), thionyl chloride (27.2 ml, 375 mmol) was added in drops. After fifteen minutes the ice bath was removed and the reaction mixture was stirred at room temperature for one hour. Then after refluxing for 48 hours, it was concentrated in vacuo. The separated crystals were filtered using methanol for washing (48.93 g). The methanolic solution on dilution with ether afforded additional 10 g of the title I compound, m.p. 208-209°.

J. N,1-Bis[(1,1-dimethylethoxy)carbonyl]-L-histidine, methyl ester

To a suspension of the title I compound (24.2 g, 100 mmol) in methanol (80 ml) were added triethyl amine (28 ml, 200 mmol) and di-tert-butyl dicarbonate (48 g, 220 mmol). After 3.5 hours, it was filtered and the methanolic solution concentrated in vacuo. The residue was taken into chloroform and washed with 10% citric acid. The crude product on crystallization from isopropyl ether afforded 23.1 g of the title J compound, m.p. 88-95° C. After evaporation and redissolution of the mother liquor (15.75 g) in methanol (50 ml) di-tert-butyl dicarbonate (10 g, 45.9 mmol) was added. After stirring the reaction mixture overnight it was evaporated, taken into chloroform and washed with 10% citric acid. The residue after chromatography over silica gel yielded 6.4 g of homogeneous title J compound.

K. N-(1,1-Dimethylethoxy)carbonyl]-3-[(phenylmethoxy)-methyl]-L-histidine, methyl ester, monohydrochloride To a solution of the title J compound (24.7 g, 66.9 mmol) in dry methylene chloride (156 ml), benzylchloromethyl ether (11.6 ml, 88.6 mmol) was added and the reaction mixture stirred at room temperature for 5 hours. After concentration in vacuo and on dissolution in ethyl acetate (100 ml), the title K compound crystallized out (17.85 g, 65%), m.p. 152°-153° C.

L. N-[(1,1-Dimethylethoxy)carbonyl]-3-[(phenylmethoxy]methyl]-L-histidine

The title K compound (18.66 g, 43.8 mmol) was dissolved in methanol (50 ml). Aqueous sodium hydroxide (1N, 92 ml) was added followed by water 83 ml). After keeping the reaction mixture at room temperature for 90 minutes it was further diluted by the addition of water (650 ml) and acidified to pH 4.5 using aqueous hydrochloric acid. The aqueous solution was extracted with chloroform. The chloroform solution was evaporated and the residue was crystallized from ethyl acetate (15.13 g, 92%), m.p. 155°-157° C.

M. (1,1-Dimethylethoxy)carbonyl]-N-(1S,2R)-1-(cyclohexylmethyl)-2-hydroxy-2-1-(phenylmethoxy)methyl]-1H-imidazol-2-yl]ethyl]-3-[(phenylmethoxy)methyl]-L-histidinamide To a solution of the title H compound (3.06 g, 7.35 mmols), 1-hydroxybenzotriazole hydrate (1.13 g, 7.35 mmols), and the title L compound (2.76 g, 7.35 mmols) in tetrahydrofuran (20 mL) were added triethylamine (2.06 mL, 14.7 mmol) and dicyclohexylcarbodiimide (1.52 g, 7.35 mmol). The mixture was stirred for 18 hours at 25° C., after which it was filtered. The filtrate was diluted with ethyl acetate, washed with saturated sodium bicarbonate solution, dried over anhydrous magnesium sulfate and concentrated. The residue (4.92 g) was chromatographed on Merck silica gel, eluting with ethyl acetate:pyridine:acetic acid:water (80:20:6:11) to give the title M compound as the major product (3.98 g, 77%).

N.
N-[(1S,2R)-1-(Cyclohexylmethyl)-2-hydroxy-2-[1-[(phenylmethoxy)methyl]-1H-imidazol-2-yl]-ethyl]-3-[(phenylmethoxy)methyl]-L-histidinamide A solution of the title M compound (3.88 g, 5.53 mmol) in ethyl acetate (200 mL) was cooled to 0° C. in an ice bath and hydrochloric acid gas was bubbled through the solution for 30 minutes. The resulting mixture was then stirred for 2.5 hours as it warmed to 25° C., after which it was concentrated to small volume. The resulting white precipitate was collected on a PTFE filter to give the title N compound as a white powder (3.33 g, 85%), m.p. 143°–157° C.

O.
]4-(4-Moroholinyl)-1,4-dioxo-2-(phenylmethyl)butyl]-N-[(1S,2R)-1-(cyclohexylmethyl)-2-hydroxy-2-1-[(phenylmethoxy)methyl]-1H-imidazol-2-yl]ethyl]-3-(phenylmethoxy)methyl]-L-histidinamide, isomer B To a mixture of the title C compound (610 mg, 2.2 mmols), 1-hydroxybenzotriazole hydrate (337 mg, 2.2 mmols) and the title N compound (1.47 g, 2 mmols) in tetrahydrofuran (8 mL) at 0° C. were added triethylamine (0.84 mL, 6 mmols) followed by dicyclohexylcarbodiimide (453 mg, 2.2 mmols). The resulting mixture was stirred for 18 hours as it warmed to 25° C., after which it was filtered. The filtrate was diluted with ethyl acetate, washed with saturated sodium bicarbonate solution, dried over anhydrous magnesium sulfate and concentrated. The mixture (1.64 g) was chromatographed on Merck silica gel (165 g), eluting with ethyl acetate:pyridine:acetic acid:water (80:20:6:11) to give isomer A of the title O compound (550 mg, 32%) and isomer B of the title O compound. The B isomer of the title O compound was further purified by preparative HPLC to give 580 mg of the title O compound.

P.
N-[(S)-2-Cyclohexyl-1-[(R)-hydroxy(1H-imidazol-2-yl)methyl]ethyl]-N2-[4-(4-morpholinyl)-1,4-dioxo-2-(phenylmethyl)butyl]-L-histidinamide, isomer B, dihydrochloride A mixture of the title O compound (isomer B) (580 mg, 0.53 mmols) 20% palladium hydroxide on carbon (120 mg), and 1N aqueous hydrochloric acid (1.17 mL, 1.17 mmols) in methanol (15 mL) was hydrogenated under a slow stream of hydrogen for 19 hours. The mixture was then filtered and concentrated to dryness. The residue (350 mg) was dissolved in 1N aqueous hydrochloric acid (10 mL) and concentrated to dryness in vacuo. The residue was redissolved in 1N hydrochloric acid and concentrated to dryness again, then was dissolved in water, millipore filtered and lyophilized to give the title compound as a fluffy white solid (330 mg, 90%).

EXAMPLE 2
4-(4-Morpholinyl)-1,4-dioxo-2-(1-naphthalenylmethyl)butyl]-N-[(1S,2R)-1-(cyclohexylmethyl)-2-hydroxy-2-(1H-imidazol-2-yl)ethyl]-L-histidinamide, isomer B, dihydrochloride

A. (1-Naphthalenylmethyl)propanedioic acid diethyl ester

To a suspension of sodium hydride (8 g of 60% dispersion in mineral oil, 200 mmols) in tetrahydrofuran (200 mL) was added diethyl malonate (30.5 mL, 200 mmols) dropwise over 15 minutes; gas evolution was observed. When the addition was complete, the mixture was stirred for 10 minutes at 25° C. A solution of 1-chloromethyl naphthalene (35.5 g, 200 mmols) in tetrahydrofuran (20 mL) was added dropwise over 15 minutes, after which the mixture was heated at reflux under argon for 18 hours. Excess 1N hydrochloric acid was then added and the mixture was extracted with ether. The extract was washed with saturated aqueous sodium bicarbonate solution, dried over anhydrous magnesium sulfate, and concentrated in vacuo. The residue was transferred to a flask fitted with a vacuum distillation head. Unreacted diethyl malonate (bp 45°–55° C./0.2 torr) and 1-chloromethyl naphthalene (bp 120°–130° C.) were distilled off and the residue was recooled to 25° C. The distillation residue (43.5 g) was crystallized from petroleum ether at −30° C. to give the title A compound as a low melting (mp about 30° C.) solid (27.3 g, 46%).

B. 1-Naphthalenepropanoic acid

A solution of the title A compound (10 g, 33.3 mmols) in ethanol (70 mL) and 1N aqueous sodium hydroxide solution (70 mL, 70 mmols) was stirred for 2 hours at 25° C. then for two hours at reflux. The ethanol was removed in vacuo and the remaining aqueous mixture was diluted with water and washed with ether. The aqueous layer was acidified by addition of 1N hydrochloric acid (100 mL). Dioxane (100 mL) was then added (for solubility) and the mixture was heated at reflux for 18 hours, after which it was concentrated in vacuo. Water and ethyl acetate were added to the residue and the mixture was extracted three times with ethyl acetate. The extract was washed with 1N hydrochloric acid, dried over anhydrous magnesium sulfate, and concentrated. The residue was triturated with ether to give the title B compound as a white solid (4.6 g, 60%), m.p. 151°–153° C.

C. 2-Naphthalenepropanoic acid, phenylmethyl ester

To a solution of the title B compound (7 g, 35 mmol), benzyl alcohol (3.8 mL, 37 mmol), and 4-dimethylamino pyridine (420 mg, 3.5 mmol) in methylene chloride (175 mL) at 0° C. was added dicyclohexylcarbodiimide (7.6 g, 37 mmol). The resulting mixture was stirred for 2 hours at 0° C. then for 18 hours at 25° C., after which it was filtered. The filtrate was washed with water and brine, dried over anhydrous magnesium sulfate, and concentrated. The residue (10.9 g) was dissolved in benzene and filtered through a pad of coarse silica gel (180 g). The filtrate was concentrated to give the title C compound as a clear, colorless oil (9.66 g, 95%).

D. (2-Naphthalenylmethyl)butanedioic acid, 4-(1,1-dimethylethyl) 1-(phenylmethyl) ester To a solution of diisopropyl amine (4.4 mL) in tetrahydrofuran (58 mL) at −10° C. under argon was added n-butyllithium (11.3 mL) of 2.6 M solution in hexane). The mixture was stirred at that temperature for 15 minutes, then was cooled to −78° C. A solution of the title C compound (8.5 g, 29 mmols) in tetrahydrofuran (10 mL) was added dropwise to the cold solution, after which the solution was stirred for 15 minutes at −78° C. Tert-butyl bromoacetate (5.2 mL, 32 mmol) was then added and the mixture was stirred for 15 minutes at −78° C., then for 2 hours as it slowly warmed to 25° C. The mixture was then poured into excess 1N hydrochloric acid and extracted with ethyl acetate. The extract was washed with saturated sodium bicarbonate solution and brine, dried over anhydrous magnesium sulfate, and concentrated. The residue (8.06 g) was flash chromatographed on silica gel (500 g), eluting first with benzene:hexanes (2:1) to bring off a yellow colored band then with benzene and finally with benzene:ethyl acetate (4:1), to give the title D compound as a colorless oil which crystallized on standing (6.62 g, 56%), m.p. 64°–66° C.

E. (2-Naphthalenylmethyl)butanedioic acid, 1-(phenylmethyl) ester

To a solution of the title D compound (9.5 g, 23.5 mmols) in methylene chloride (50 mL) at 0° C. was added trifluoroacetic acid (50 mL). The mixture was stirred for 2 hours at 0° C., after which it was concentrated to dryness. The residue was crystallized from acetonitrile to give the title E compound (6.89 g, 84%), m.p. 124°–126° C.

F. (2-Naphthalenylmethyl)butanedioic acid, 1-(phenylmethyl) ester, (+)-isomer The title E compound (5.8 g, 16.6 mmol) was dissolved in ether (100 mL) and (−)-ephedrine (2.75 g, 16.6 mmol) was added. The mixture was stored at −30° C. for three days resulting in a waxy solid which was collected. The solid was recrystallized twice from 35 mL of ethyl acetate and 165 mL of ether, then twice more from 50 mL of ethyl acetate and 150 mL of ether, resulting in a solid of constant melting point and specific rotation (3.0 g, m.p. 114.5°–115.5° C., $[\alpha]D = +31.7°$). The crystalline solid was then partitioned between ethyl acetate and 1N hydrochloric acid and was extracted with ethyl acetate. The extract was dried and concentrated to give the title F compound, $[\alpha]_D = +54.8°$ (methanol), (1.89 g).

G. α-(2-Naphthalenylmethyl)-γ-oxo-4-morpholinebutanoic butanoic acid, phenylmethyl ester, (+)-isomer To a mixture of the title F compound (1.89 g, 5.4 mmol, $[\alpha]_D = +54.8°$), morpholine (0.525 mL, 6 mmols), and 1-hydroxybenzotriazole (730 mg, 5.4 mmol) in tetrahydrofuran (15 mL) was added dicyclohexylcarbodiimide (1.1 g, 5.4 mmol). The resulting mixture was stirred at 25° C. for 20 hours, after which it was filtered. The filtrate was diluted with ethyl acetate, washed with 1N hydrochloric acid and saturated sodium bicarbonate solution, dried over anhydrous magnesium sulfate, and concentrated to give the title G compound (2.1 g, 93%). $[\alpha]_D = +32.1°$ (c 4, methanol).

H. α-(2-Naphthalenylmethyl)-γ-oxo-4-morpholine butanoic acid, (−)-isomer

A mixture of the title G compound (2.1 g, 5 mmol) and 1N sodium hydroxide solution (5 mL) in dioxane (10 mL) was stirred at 25° C. for 16 hours, after which it was diluted with water and washed with ether. The aqueous layer was acidified (HCl) and extracted three times with ethyl acetate. The extract was dried over anhydrous magnesium sulfate and concentrated to give the title H compound as a colorless glass (1.58 g, 97%).

I. [R-(R*,S*)]-N-[1-(Cyclohexylmethyl)-2-hydroxy-2-(1H-imidazol-2-yl)ethyl]-L-histidinamide A mixture of the title M compound from Example 1 (1.46 g, 2 mmols), 20% palladium hydroxide on carbon (350 mg, Aldrich), and 1N hydrochloric acid (4 mL, 4 mmols) in methanol (15 mL) was hydrogenated under a slow stream of hydrogen for 20 hours at 25° C., after which it was filtered (PTFE filter) and concentrated to dryness. The residue (1.1 g) was dissolved in acetic acid (30 mL) and dry hydrochloric acid gas was bubbled through the solution for 30 minutes at 25° C. The mixture was then stirred at 25° C. for two hours, after which it was concentrated in vacuo. The residue was triturated with acetonitrile to give a white solid (833 mg). The solid was dissolved in excess 1N hydrochloric acid and was concentrated to dryness; the process was repeated a total of three times to give the title I compound as a white solid.

J. [4-(4-Morpholinyl)-1,4-dioxo-2-(1-naphthalenylmethyl)butyl]-N-[(1S,2R)-1-(cyclohexylmethyl)-2-hydroxy-2-(1H-imidazol-2-yl)ethyl]-L-histidinamide, isomer B, dihydrochloride To a solution of the title H compound (164 mg, 0.5 mmol), 1-hydroxybenzotriazole hydrate (84 mg, 0.55 mmol) and the title I compound (276 mg, 0.55 mmol) in dimethylformamide (2.5 mL) at 0° C. were added triethylamine (0.24 mL, 1.65 mmol) and dicyclohexylcarbodiimide (113 mg, 0.55 mmol). The resulting mixture was stirred for 18 hours as it warmed to 25° C., after which the mixture was concentrated to dryness in vacuo. The residue was dissolved in a mixture of methanol (3 mL) and 1N hydrochloric acid (2 mL), filtered, and concentrated. The residue (814 mg) was chromatographed on Merck silica gel, eluting with ethyl acetate:pyridine:acetic acid:water (50 20:6:11). Fractions containing the major product ($R_f$ 0.25) were combined and concentrated. The residue was dissolved in excess 1N hydrochloric acid and concentrated to dryness three times. The reddish residue (295 mg, 74%) was chromatographed on HP-20, eluting with a gradient from 0.01N hydrochloric acid to methanolic hydrochloric acid (0.01N). Fractions containing the major product were combined and partially concentrated, then lyophilized to dryness. The residue was relyophilized from water to give the title compound as a fluffy white solid (120 mg, 29%).

EXAMPLE 3

[4-Cyclohexyl-1,4-dioxo-2-(phenylmethyl)butyl]-N-[(2S,3R)-1-(cyclohexylmethyl)-2-hydroxy-2-(1H-imidazol-2-Y1)ethyl]-L-histidinamide, isomer B, dihydrochloride

A. (2-Cyclohexyl-2-oxoethyl)(phenylmethyl)propanedioic acid, diethyl ester

To a suspension of sodium hydride (8 g, 0.2 mole) in tetrahydrofuran (200 mL) under argon was added diethylbenzyl malonate (50 g, 0.2 mole). The mixture was stirred for 30 minutes at 25° C. after the addition was complete, resulting in a homogeneous solution. Bromomethyl cyclohexyl ketone (20.5 g, 0.1 mole; the preparation of which has been described in *Tetrahedron Letters*, 26, 5611–5615, (1970)) was then added over 10 minutes, after which the mixture was warmed to 50° C. and stirred at that temperature for 16 hours. The mixture was then poured into excess 1N hydrochloric acid and the resulting mixture was extracted with ether. The extract was washed once in 1N hydrochloric acid and twice in sodium hydrogen carbonate, dried over anhydrous magnesium sulfate and concentrated to a yellow oil. The oil was distilled and the residue passed through a short column of silica gel, using stepwise gradient elution. Elution with 1:1 hexane:ethyl acetate gave the title B compound as a yellowish oil (28 g, 75%).

B. α-(Phenylmethyl)-γ-oxocyclohexanebutanoic acid

A mixture of the title A compound (28 g, 0.075 mmol) and 1N sodium hydroxide solution (150 mL, 0.15 mole) in ethanol (150 mL) was stirred at 75° C. for 15 hours, after which it was diluted with water (500 mL) and washed with ether. The aqueous solution was then acidified in concentrated hydrochloric acid and extracted twice with ethyl acetate. The extract was dried and concentrated to a yellow oil (18 g). The residue was dissolved in dioxane (180 mL), concentrated hydrochloric acid (1 mL) was added, and the mixture was stirred at 100° C. for 22 hours. The mixture was then concentrated to an orange oil. The oil was dissolved in 1N sodium hydroxide solution (125 mL) and the mixture was stirred for 18 hours at 75° C., after which it was diluted with water and washed with ether. The aqueous solution was made acidic with hydrochloric acid and extracted twice with ether. The extract was dried over anhydrous magnesium sulfate and concentrated to give a yellow oil (12 g). After standing at 25° C. for one week, the compound crystallized. The crystals were triturated with petroleum ether to give the title B compound as a white powder (8.4 g, 41%), m.p. 71°–73° C.

C.
4-Cyclohexyl-1,4-dioxo-2-(phenylmethyl)butyl]-N-[(2S,3R)-1-(cyclohexylmethyl)-2-hydroxy-2-(1H-imidazol-2-yl)ethyl]-L-histidinamide, isomer B, dihydrochloride To a solution of the title I compound from Example 2 (754 mg, 1.5 mmols) 1-hydroxybenzotriazole hydrate (230 mg, 1.5 mmols), and the title B compound (230 mg, 1.5 mmols) in dimethylformamide (7 mL) at 0° C. were added triethylamine (0.68 mL, 4.9 mmols) and dicyclohexylcarbodiimide (309 mg, 1.50 mmols). The resulting mixture was stirred for 18 hours at 25° C., after which it was concentrated to dryness. Methanol (9 mL) and 1N hydrochloric acid (6 mL) were added to the residue. The resulting solution was filtered and the filtrate was concentrated to dryness. The residue (2.56 g) was chromatographed on Merck silica gel; fractions containing the major product ($R_f$ 0.2) were collected and concentrated. The residue (640 mg) was further purified by preparative HPLC. Two major fractions (Isomer A and Isomer B) were separately collected and concentrated. The resulting trifluoroacetate salts were not water soluble, thus the residues were separately dissolved in excess 1N hydrochloric acid and reconcentrated three times to convert to the soluble hydrochloride salts. The residues were then dissolved in water, charcoal filtered, and lyophilized to give Isomer A (162 mg, 16=%) and Isomer B (134 mg, 13%) of the title compound.

EXAMPLE 4

[3-[(Cyclohexylthio)methyl]-1-oxo-3-phenylpropyl]-N-[(1S,2R)-1-(cyclohexylmethyl)-2-hydroxy-2-(1H-imidazol-2-yl)ethyl]-L-histidinamide, dihydrochloride α-Methylenebenzenepropanoic acid Benzyl malonic acid (13 g, 0.067 mole) was mixed with aqueous dimethylamine (7.6 g. 0.068 mole, 40%) and formalin (5.4 g, 0.068 mole, 37%) in water (150 ml). The voluminous solid which formed in 15 minutes was filtered after 2 hours, washed with water and dried partially in air to give 20.8 g. The solid was melted in a 170° oil bath and heated for 10 minutes, until amine evolution had stopped and bubbling had virtually ceased. The cooled product, a mobile liquid, was acidified with 10% potassium hydrogen sulfate, extracted with hexane, dried over sodium sulfate and evaporated to give 6.3 g of solid. The aqueous filtrates from the Mannich reaction were allowed to stand overnight and were then heated at 100° C. on a steam cone until bubbling ceased. Cooling, acidification and extraction as above gave another 1.2 g of solid for a total of 7.5 g of benzyl acrylic acid.

B. α-[(Cyclohexylthio)methyl]benzenepropanoic acid

To a solution of the title A compound (8.1 g, 50 mmol) in piperidine (16 mL) under argon was added cyclohexyl mercaptan (6 mL, 50 mmol). The mixture was stirred under argon at 100° C. for 24 hours, after which it was cooled to 25° C. and acidified by addition of concentrated hydrochloric acid. The mixture was then saturated with sodium chloride and was extracted twice with ether. The ether extracts were combined and extracted with 1N sodium hydroxide solution. The basic aqueous extract was made acidic by addition of concentrated hydrochloric acid and was extracted with ethyl acetate. The extract was dried over anhydrous magnesium sulfate and concentrated. The residue (4 g) was purified by flash chromatography on silica gel, eluting with 1:1 ethyl acetate:hexanes, to give the title B compound as a colorless oil.

C.
3-(Cyclohexylthio)methyl]-1-oxo-3-phenylpropyl]-n-[(1S,2R)-1-(cyclohexylmethyl)-2-histidinamide, dihydrochloride To a solution of the title B compound (557 mg, 2 mmol), 1-hydroxybenzotriazole hydrate (337 mg, 2.2 mmol) and the title I compound from Example 2 (1.1 g, 2.2 mmol) in dimethylformamide (8 mL) at 0° C. were added triethylamine (0.92 mL, 2.2 mmol) and dicyclohexylcarbodiimide (453 mg, 2.2 mmol). The resulting mixture was stirred for 18 hours at 25° C., after which it was concentrated to dryness. The residue was dissolved in a mixture of methanol (9 mL) and 1N hydrochloric acid (6 mL), filtered, and the filtrate was concentrated to dryness. The residue (3.68 g) was flash chromatographed on silica gel, eluting with ethyl acetate:pyridine: acetic acid:water (80:20:6:11) to yield a major fraction having $R_f$=0.31 (940 mg). This pinkish material was further purified by chromatography on HP-20 (400 mL), eluting with a gradient from 0.01 N hydrochloric acid to 0.01 N hydrochloric acid in methanol. Fractions were monitored by HPLC analysis; those containing the desired products (7.1 min and 8.3 min. YMC S-ODS column, 4.6×150 mm, 1.0 mL/min of 66% aqueous methanol containing 0.01% phosphoric acid, λ=220 nm) were combined and partially concentrated in vacuo to remove methanol, then frozen and lyophilized. The residue was relyophilized from water to give the title compound as a fluffy, off-white (pinkish) solid (386 mg, 28%).

EXAMPLE 5

2-[(Cyclohexylsulfinyl)methyl]-1-oxo-3-phenylpropyl]-N-(1S,2R)-1-(cyclohexylmethyl)-2-hydroxy-2-(1H-imidazol-2-yl)-ethyl-L-histidinamide, isomer 2B, trifluoroacetate (1:2) salt A. α-[(Cyclohexylsulfinyl)methyl]benzenepropanoic acid, isomers 1 and 2

A solution of the title B compound from Example 4 (1.95 g, 7 mmol) and hydrogen peroxide (4.76 mL, 42 mmol) in methanol (35 mL) was stirred at 25° C. for two hours, after which additional hydrogen peroxide was added (0.45 mL). The mixture was stirred for 1.5 additional hours (3.5 hours total), then made acidic by addition of sulfuric acid (35 mL). The mixture was checked for presence of peroxides using starch-iodine test paper (positive test). Saturated aqueous sodium thiosulfate solution was added until a positive peroxide test was no longer obtained. The mixture was then diluted with an equal volume of ethyl acetate and stirred for 10 minutes, after which it was filtered and extracted with ethyl acetate. The extracts were combined, dried over anhydrous magnesium sulfate, and concentrated. The residue (2.3 g) was crystallized from 95% ethanol to give isomer 1 of the title A compound (670 mg, 32%, m.p. 153°-154° C.). The mother liquor was diluted with ether and cooled to give a white solid (m.p. 118°-120° C.) which was recrystallized from ethanol to give isomer 2 of the title A compound (365 mg, 18%, m.p. 123°-124° C.).

B.
[2-[(Cyclohexylsulfinyl)methyl]-1-oxo-3-phenylpropyl]-N-[(1S,2R)-1-(cyclohexylmethyl)-2-hydroxy-2-(1H-imidazol-2-yl)-ethyl]-L-histidinamide, isomer 2B, trifluoroacetate (1:2) salt To a solution of the isomer 2 of the title A compound (539 mg, 1.83 mmol), 1-hydroxybenzotriazole hydrate (306 mg, 2 mmol), and the title I compound from Example 2 (998 mg, 2 mmol) in dimethylformamide (7 mL) at 0° C. were added triethylamine (0.85 mL, 6 mmol) and dicyclohexylcarbodiimide (412 mg, 2 mmol). The resulting mixture was stirred for 19 hours at 25° C., after which it was concentrated to dryness. The residue was dissolved in a mixture of methanol (10 mL) and 1N hydrochloric acid (7 mL), filtered and concentrated. The residue (3.6 g) was flash chromatographed on silica gel, eluting with ethyl acetate:(pyridine:acetic acid:water) 2:1(20:6:11). Fractions containing the major "product" (R$_f$0.30) were combined and concentrated to give an isomeric mixture (720 mg). The isomers were separated by preparative HPCL to give isomer 2A of the title B compound (280 mg, 31%) and isomer 2B of the title B compound (150 mg, 17° %).

EXAMPLE 6

[2-[(Cyclohexylsulfonyl)methyl]-1-oxo-3-phenylpropyl]-N-[(1S,2R)-1-(cyclohexylmethyl)-2-hydroxy-2-(1H-imidazol-2-yl)-ethyl]-L-histidinamide, isomer B, trifluoroacetate (1:2) salt A. α-(Cyclohexylsulfonyl)methyl]benzenepropanoic acid To a solution of the title B compound from Example 4 (2.78 g, 10 mmol) in methanol (40 mL) at 0° C. was added a solution of potassium monopersulfate (9.21 g, 30 mmol) in water (40 mL). The resulting mixture was stirred for 2 hours as it warmed to 25° C., after which it was extracted with chloroform. The extract was dried over anhydrous magnesium sulfate and concentrated. The residue (3.02 g) was crystallized from ethyl acetate/hexanes to give the title A compound (2.90 g, 94%), m.p. 109°-111° C.

B.
2-(Cyclohexylsulfonyl)methyl]-1-oxo-3-phenylpropyl]-N-(1S,2R)-1-(cyclohexylmethyl)-2-hydroxy-2-(1H-imidazol-2-yl)-ethyl]-L-histidinamide, isomer B, trifluoroacetate (1:2) salt To a solution of the title A compound (1.24 g, 4 mmol), 1-hydroxybenzotriazole hydrate (612 mg, 4 mmol) and the title I compound from Example 2 (2 g, 4 mmol) in dimethylformamide (15 mL) at 0° C. were added triethylamine (1.76 mL, 12.6 mmol) and dicyclohexylcarbodiimide (824 mg, 4 mmol). After being stirred for 18 hours at 25° C., the mixture was concentrated to dryness. To the residue were added methanol (20 mL) and 1N hydrochloric acid (14 mL). The mixture was filtered and the filtrate was concentrated to dryness. The residue was chromatographed on silica gel to give an isomeric mixture R$_f$0.28 (1.54 g). The isomers were separated by preparative HPLC. Fractions containing the individual isomers were partially concentrated and lyophilized. The residues were relyophilized from water to give isomer A of the title B compound (730 mg, 21%) and isomer B of the title B compound (520 mg, 15° %).

EXAMPLE 7

[2-[(Diethoxyohosphinyl)methyl]-1-oxo-3-phenylpropyl]-N-[(2S,3R)-1-(cyclohexylmethyl)-2-hydroxy-2-(1H-imidazol-2-yl)ethyl-L-histidinamide, isomer B, trifluoroacetate (1:2) salt A. α-[(Diethoxyphosphinyl)methyl]benzenepropanoic acid Bis(trimethylsilyl)acetamide (5 g, 0.024 mole, 6 ml) was added, at room temperature, to a solution of benzyl acrylic acid (2 g, 0.012 mole) and diethyl phosphite (3.3 g, 0.024 moles) in dichloromethane (30 ml). The mixture was stirred at ambient temperature for 30 minutes, concentrated in vacuo at room temperature, and the residue was heated at a bath temperature of 100°-110° for 16 hours. The colorless oil reaction mixture was dissolved in ethyl acetate and extracted with 5% sodium bicarbonate (pH 9-10). The aqueous alkaline solution was washed with ether and acidified to a pH of 1-2 with concentrated hydrochloric acid. The colorless oil that separated was extracted into ethyl acetate, washed with brine, dried over anhydrous magnesium sulfate and concentrated in vacuo to give a colorless oil (3.6 g).

B.
[2-[(Diethoxyphosohinyl)methyl]-1-oxo-3-phenyl-propyl]-N-[(1S,2R)-1-(cyclohexylmethyl)2-hydroxy-2-[1-[(phenylmethoxy)methyl]-1H-imidazol-2-yl]ethyl]-3-[(phenylmethoxy)methyl]-L-histidinamide, isomers A and B To a solution of the title J compound from Example 1 (1.46 g, 2.0 mmols), 1-hydroxybenzotriazole hydrate (337 mg, 2.20 mmols), and the title A compound (600 mg, 2.20 mmols) in tetrahydrofuran (8 mL) at 0° C. were added triethylamine (0.92 mL, 6.6 mmols) and dicyclohexylcarbodiimide (453 mg, 2.20 mmols). The resulting mixture was stirred for 18 hours at 25° C. and filtered. Ethyl acetate was added to the filtrate and the resulting solution was washed with saturated sodium bicarbonate solution, dried over anhydrous magnesium sulfate and concentrated. The residue (1.75 g) was flash chromatographed on Merck silica gel, eluting with ethyl acetate:pyridine:acetic acid:water (100:20:6:11), to give isomer A of the title B compound (680 mg, 38%) and isomer B of the title B compound (620 mg, 35%).

C.
[2-[(Diethoxyphosohinyl)methyl]-1-oxo-3-phenyl-prooyl]-N-(2S,3R)-1-(cyclohexylmethyl)-2-hydroxy-2-(1H-imidazol-2-yl)ethyl- L-histidinamide, isomer B, trifluoroacetate (1:2) salt A mixture of the isomer B of the title B compound (600 mg, 0.68 mmols), 20% palladium hydroxide on carbon (150 mg), and 1N hydrochloric acid (1.5 mL, 1.5 mmols) in methanol (15 mL) was hydrogenated under a slow stream of hydrogen for 18 hours at 25° C., after which it was filtered and concentrated to dryness. The residue (470 mg) was flash chromatographed on Merck silica gel, eluting with chloroform:methanol:ammonium hydroxide (100:25:1.25). Fractions containing the major component were combined and concentrated. The residue (300 mg) was dissolved in excess 1% aqueous trifluoroacetic acid solution and reconcentrated. The residue was then dissolved in water (50 mL), treated with activated charcoal, millipore filtered, and lyophilized to give the title compound as a fluffy white solid (320 mg, 66%).

EXAMPLE 8
[(S)-2-[(Benzoylthio)methyl]-1-oxo-3-phenylpropyl]-N-[(1S,2R)-1-(cyclohexylmethyl-2-hydroxy-2-(1H-imidazol-2-yl)ethyl]-L-histidinamide, trihydrochloride A. α-[(Benzoylthio)methyl]benzenepropanoic acid A mixture of the title A compound from Example 4 (13.7 g, 85 mmol) and thiobenzoic acid (15 mL, 127 mmol) in methylene chloride (170 mL) was stirred under argon at reflux temperature for 3 days, after which it was concentrated in vacuo. The residue was crystallized from ether/hexane to give 13.7 g of the title A compound as a colorless solid, m.p. 99°–100° C.

B. (S)-α-[(Benzoylthio)methyl]benzenepropanoic acid

A solution of the title A compound (14.5 g, 48.0 mmol) and (R)-(+)-α-methylbenzyl amine (6.25 mL, 48 mmol) in ether (250 mL) was stored at −4° C. for two days, resulting in a gummy solid. The solvent was decanted and the solid was recrystallized 3 times from hexane/methylene chloride (1:1) then twice from isopropanol to give a 1:1 salt, m.p. 131°–132° C., $[\alpha]_D = -25.0°$ (c = 1, CHCl$_3$). The salt was dissolved in ethyl acetate and washed with 1.0 N hydrochloric acid. The organic layer was dried over anhydrous magnesium sulfate and concentrated to give 1.57 g of the title B compound as a white solid, m.p. 65°–66° C., $[\alpha]_D = -53.3°$ (c = 1, CHCl$_3$).

C.
[(S)-2-[(Benzoylthio)methyl]-1-oxo-3-phenylpropyl]-N-[(1S,2R)-1-(cyclohexylmethyl-2-hydroxy-2-(1H-imidazol-2-yl)ethyl]-L-histidinamide, trihydrochloride To a solution of the title B compound (1.42 g, 4.73 mmol), 1-hydroxybenzotriazole hydrate (724 mg, 4.73 mmol) and the title I compound from Example 2 (2.22 g) in dimethylformamide (20 mL) at 0° C. were added triethylamine (2.2 mL, 16 mmol) and dicyclohexylcarbodiimide.(975 mg, 4.73 mmol). The resulting mixture was stirred at 25° C. for 18 hours, after which it was filtered and concentrated. The residue was chromatographed on silica gel, eluting with ethyl acetate:(-pyridine:acetic acid:water) 2:1(20:6:11). Fractions containing the major product were combined and concentrated. The residue was dissolved in excess 1N hydrochloric acid and concentrated in vacuo. The residue was then lyophilized from water to give the title compound as a fluffy white solid.

EXAMPLE 9
[(S)-2-(Mercaptomethyl)-1-oxo-3-phenylpropyl]-N-[(1S,2R)-1-(cyclohexylmethyl)2-hydroxy-2-(1H-imidazol-2-yl)ethyl]-L-histidinamide, trifluoroacetate (1:2) salt A mixture of [(S)-2-[(benzoylthio)methyl]-1-oxo-3-phenylpropyl]-N-[(1S,2R)-1-(cyclohexylmethyl-2-hydroxy-2-(1H-imidazol-2-yl)ethyl]-L-histidinamide, trihydrochloride (270 mg, 0.35 mmol) and concentrated ammonium hydroxide solution (1 mL) in methanol (5 mL) was stirred at 50° C. for 7 days (additional ammonium hydroxide (2 mL) was added after 2 and 6 days). After 7 days, the mixture was concentrated in vacuo and the residue was purified by preparative HPLC. Fractions containing the major product were concentrated in vacuo. The residue was dissolved in water and lyophilized to give 45 mg of the title compound as a fluffy white powder.

EXAMPLES 10–30

Following the procedures of Examples 1–9, additional compounds within the scope of this invention can be prepared having the formula

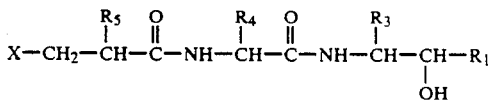

wherein the substituents are as defined below.

| Ex. No. | X | R₅ | R₄ | R₃ | R₁ |
|---|---|---|---|---|---|
| 10 | (CH₃)₃C—CO— | —CH₂—C₆H₅ | —CH₂-(imidazolyl-NH) | —CH₂—C₆H₅ | N-methyl imidazolyl |
| 11 | C₆H₅—CH₂—O—C(=O)— | —CH₂—C₆H₅ | —CH₂-(imidazolyl-NH) | —CH₂—cyclohexyl | 2-methyl imidazolyl-NH |
| 12 | naphthyl-CH₂—O—C(=O)— | —CH₂-naphthyl | —CH₂-(imidazolyl-NH) | —CH₂CH(CH₃)₂ | imidazolyl-NH |
| 13 | (CH₃)₃C—SO₂— | —CH₂-pyridyl | —CH₂—C₆H₅(NH) | —CH₂CH(CH₃)₂ | imidazolyl-NH |
| 14 | morpholinyl-SO₂— | —CH₂—C₆H₅ | —CH₂-(imidazolyl-NH) | —CH₂CH(CH₃)₂ | oxazolyl |
| 15 | (CH₃)₂CH—SO₂— | —CH₂CH₂—C₆H₅ | —CH₂—C₆H₅ | —CH(CH₃)₂ | thiazolyl |
| 16 | (CH₃CH₂O)₂P(=O)— | —CH₂-(C₆H₄-NH) | —CH₂-(imidazolyl-NH) | —CH₂CH(CH₃)₂ | oxazolyl |

-continued

| Ex. No. | X | R$_5$ | R$_4$ | R$_3$ | R$_1$ |
|---|---|---|---|---|---|
| 23 | (CH$_3$)$_3$C—S(=O)$_2$— | —CH$_2$-phenyl | —CH$_2$-phenyl | —CH$_2$-(imidazole) | 2-methylpyridine |
| 24 | cyclohexyl-S(=O)$_2$— | —CH$_2$-naphthyl | —CH$_2$-(imidazole) | —CH$_2$CH(CH$_3$)$_2$ | H—N=C(CH$_2$-phenyl)-imidazole |
| 25 | (CH$_3$)$_2$N—S(=O)$_2$— | —CH$_2$-phenyl | —CH$_2$-(imidazole) | —CH$_2$CH(CH$_3$)$_2$ | H—N=C(CH$_2$-cyclopentyl)-imidazole |
| 26 | CH$_3$CH$_2$—P(=O)(CH$_2$CH$_3$)— | —CH$_2$-(p-phenyl) | —CH$_2$-(imidazole) | —CH$_2$CH(CH$_3$)$_3$ | H—N—CH(C$_2$H$_5$)—CH$_2$—imidazole |
| 27 | H—S | —CH$_2$-(p-phenyl) | —CH$_2$-(imidazole) | —CH$_2$-cyclohexyl | H—N-(2-methylphenyl) |
| 28 | phenyl-C(=O)—S— | —CH$_2$-(p-phenyl) | —(CH$_2$)$_4$—NH$_2$ | —CH$_2$-cyclohexyl | imidazole (N—H) |

-continued

| Ex. No. | X | R₅ | R₄ | R₃ | R₁ |
|---|---|---|---|---|---|
| 29 | H—S | —CH₂—(phenyl) | —CH₂—(CH=N–CH=CH–NH) | —CH₂—(cyclohexyl) | (CH=N–CH=CH–S) |
| 30 | (CH₃)₃C—CH₂—P(=O)(OCH₂CH₃) | —CH₂—(phenyl) | —CH₂—(CH=N–CH=CH–NH) | —CH₂—(cyclohexyl) | (CH=N–CH=CH–O) |

What is claimed is:
1. A compound having the formula

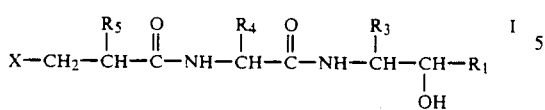

or pharmaceutically acceptable salts thereof, wherein X is selected from

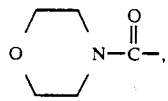

$R_1$ is selected from

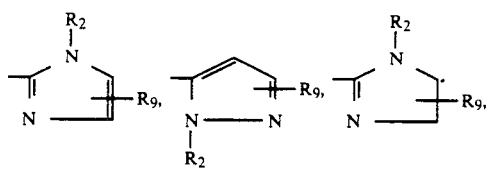

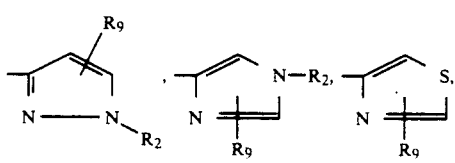

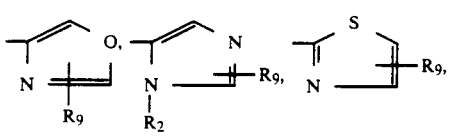

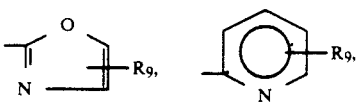

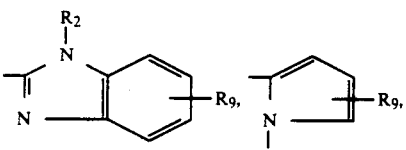

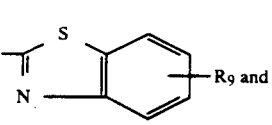

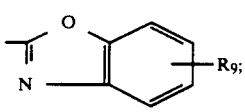

$R_2$ is

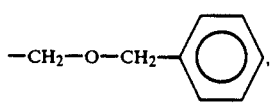

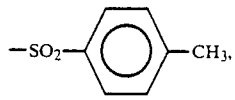

2,4-dinitrophenyl, hydrogen, lower alkyl,

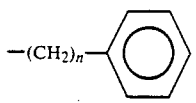

or —$(CH_2)_n$-cycloalkyl;

$R_3$ and $R_5$ are independently selected from hydrogen, lower alkyl, halo substituted lower alkyl, —$(CH_2)_n$-aryl, —$(CH_2)_n$—OH, —$(CH_2)_n$—O—lower alkyl, —$(CH_2)_n$—$NH_2$, —$(CH_2)_n$—SH, —$(CH_2)_n$—S—lower alkyl, —$(CH_2)_n$—O—$(CH_2)_g$—OH, —$(CH_2)_n$—O—$(CH_2)_g$—$NH_2$, —$(CH_2)_n$—S—$(CH_2)_g$—OH, —$(CH_2)_n$—$\overset{O}{\overset{\|}{C}}$—OH, —$(CH_2)_n$—S—$(CH_2)_g$—$NH_2$, —$(CH_2)_n$—NH—$\overset{NH}{\overset{\|}{C}}$—$NH_2$, —$(CH_2)_n$—$\overset{O}{\overset{\|}{C}}$—$NH_2$, —$(CH_2)_n$—[imidazole]—N—$R_7$, —$(CH_2)_n$—[imidazole]—N, and —$(CH_2)_n$—cycloalkyl;
$R_4$ is selected from hydrogen, lower alkyl, halo substituted lower alkyl, —$(CH_2)_n$—aryl, —$(CH_2)_n$—OH, —$(CH_2)_n$—O—lower alkyl, —$(CH_2)_n$—$NH_2$, —$(CH_2)_n$—SH, —$(CH_2)_n$—S—lower alkyl, —$(CH_2)_n$—O—$(CH_2)_g$—OH, —$(CH_2)_n$—O—$(CH_2)_g$—$NH_2$, —$(CH_2)_n$—S—$(CH_2)_g$—OH, —$(CH_2)_n$—$\overset{O}{\overset{\|}{C}}$—OH, —$(CH_2)_n$—S—$(CH_2)_g$—$NH_2$, —$(CH_2)_n$—NH—$\overset{NH}{\overset{\|}{C}}$—$NH_2$, —$(CH_2)_n$—$\overset{O}{\overset{\|}{C}}$—$NH_2$, —$(CH_2)_n$—[imidazole]—N—$R_7$, —$(CH_2)_n$—[imidazole]—N, —$(CH_2)_n$—cycloalkyl, —$(CH_2)_n$—[imidazole N—$R_7$], -continued

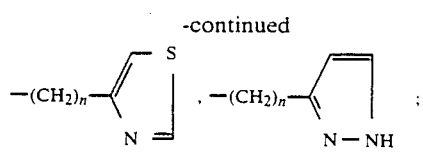

n is an integer from 1 to 5;
g is an integer from 2 to 5;
R₇ is

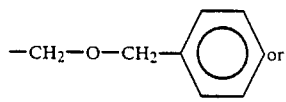

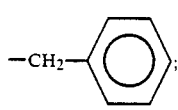

R₈ is 2,4-dinitrophenyl

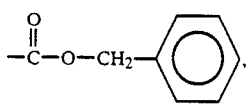

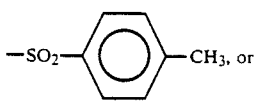

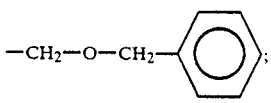

and
R₉ is hydrogen, lower alkyl,

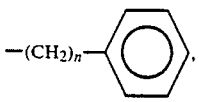

or —(CH₂)ₙ-cycloalkyl.

2. A compound in accordance with claim 1 wherein X is

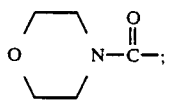

R₁ is

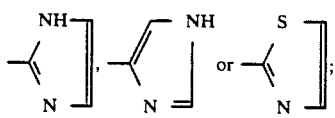

R₃ is straight or branched chain lower alkyl of 3 to 5 carbons, —(CH₂)ₙ-cyclopentyl, —(CH₂)ₙ-cyclohexyl, or

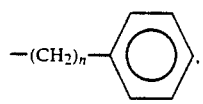

wherein n is an integer from 1 to 3;
R₄ is hydrogen, straight or branched chain lower alkyl of up to 5 carbons, —(CH₂)₄—NH₂,

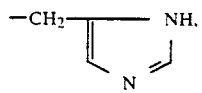

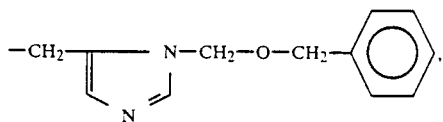

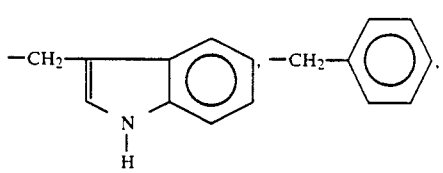

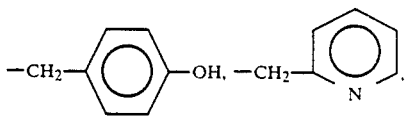

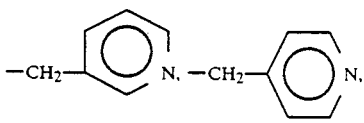

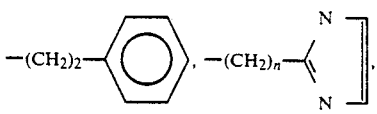

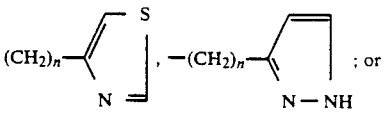

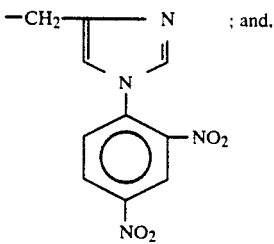

R₅ is straight or branched chain lower alkyl of up to 5 carbons,

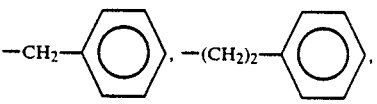

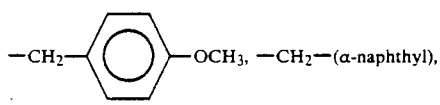

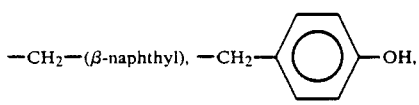

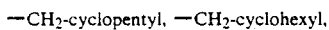

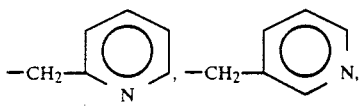

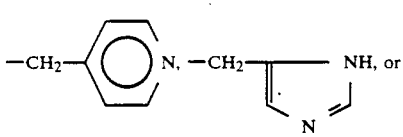

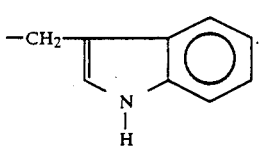

3. A compound in accordance with claim 1 wherein R₁ is

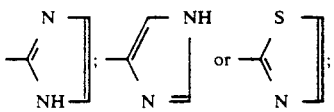

R₃ is

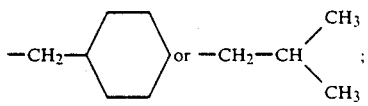

R₄ is

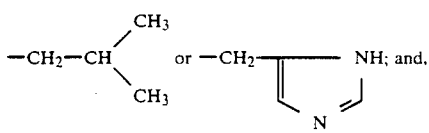

and, R₅ is

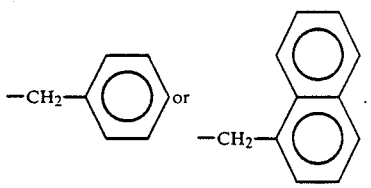

4. Compound in accordance with claim 1 having the name [4-(4-morpholinyl)-1,4-dioxo-2-(1-naphthalenyl-methyl)butyl]-N-[(1S,2R)-1-(cyclohexylmethyl)-2-hydroxy-2-(1H-imidazol-2-yl)ethyl]-L-histidinamide, isomer B, dihydrochloride.

5. A compound in accordance with claim 1 having the name N-[(S)-2-cyclohexyl-1-[(R)-hydroxy-(1H-imidazol-2-yl)methyl]ethyl]-N2-[4-(4-morpholinyl)-1,4-dioxo-2-(phenylmethyl)butyl]-L-histidinamide, isomer B, dihydrochloride.

6. A composition for treating hypertension in a mammalian species comprising a pharmaceutically acceptable carrier and an anti-hypertensively effective amount of a compound of claim 1.

7. A method of treating hypertension in a mammalian species which comprises administering an anti-hypertensively effective amount of the composition of claim 6.

* * * * *